(12) United States Patent
Roberts et al.

(10) Patent No.: US 10,825,353 B2
(45) Date of Patent: Nov. 3, 2020

(54) DEVICE FOR ENHANCEMENT OF LANGUAGE PROCESSING IN AUTISM SPECTRUM DISORDERS THROUGH MODIFYING THE AUDITORY STREAM INCLUDING AN ACOUSTIC STIMULUS TO REDUCE AN ACOUSTIC DETAIL CHARACTERISTIC WHILE PRESERVING A LEXICALITY OF THE ACOUSTICS STIMULUS

(71) Applicants: The Children's Hospital of Philadelphia, Philadelphia, PA (US); The Trustees of the University of Pennsylvania, Philadelphia, PA (US)

(72) Inventors: Timothy Roberts, Philadelphia, PA (US); David Embick, Philadelphia, PA (US)

(73) Assignees: The Children's Hospital of Philadelphia, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 266 days.

(21) Appl. No.: 14/910,922

(22) PCT Filed: Aug. 13, 2014

(86) PCT No.: PCT/US2014/050893
§ 371 (c)(1),
(2) Date: Feb. 8, 2016

(87) PCT Pub. No.: WO2015/023751
PCT Pub. Date: Feb. 19, 2015

(65) Prior Publication Data
US 2016/0210872 A1    Jul. 21, 2016

Related U.S. Application Data

(60) Provisional application No. 61/865,293, filed on Aug. 13, 2013.

(51) Int. Cl.
*G09B 19/00* (2006.01)
*A61B 5/00* (2006.01)
(Continued)

(52) U.S. Cl.
CPC ............... *G09B 19/00* (2013.01); *A61B 5/05* (2013.01); *A61B 5/4803* (2013.01); *G09B 5/04* (2013.01);
(Continued)

(58) Field of Classification Search
CPC .......... G09B 19/00; G09B 19/04; G09B 5/04; G09B 23/28; A61B 5/05; A61B 5/168;
(Continued)

(56) References Cited

U.S. PATENT DOCUMENTS 5,813,862 A    9/1998  Merzenich et al.
8,940,732 B2 *  1/2015  Page .................... A61K 31/403
                                                          435/6.16
(Continued)

FOREIGN PATENT DOCUMENTS

JP    10511472 A    11/1998
JP    2008186010 A   8/2008
(Continued)

OTHER PUBLICATIONS

International Search Report for International Application No. PCT/US2014/050893 dated Nov. 21, 2014.
(Continued)

*Primary Examiner* — Bharatkumar S Shah
(74) *Attorney, Agent, or Firm* — RatnerPrestia

(57) ABSTRACT

Methods and devices can enhance language processing in an autism spectrum disorder (ASD) individual through auditory manipulation of an auditory stream. The auditory stream is received and includes an acoustic stimulus perceptually representing an object. An acoustic manipulation parameter
(Continued)

for a predetermined acoustic detail characteristic is selected. The predetermined acoustic detail characteristic is associated with the ASD individual and is based on a measured language processing capability of the ASD individual. The auditory stream is modified based on the selected parameter, to reduce the predetermined acoustic detail characteristic while preserving a lexicality of the stimulus, such that the reduced acoustic detail characteristic enhances perception of the object by the ASD individual even when the stimulus includes two or more acoustically distinct stimuli each perceptually representing the object. The modified auditory stream is output to the ASD individual via at least one loudspeaker.

22 Claims, 4 Drawing Sheets

(51) Int. Cl.

| | | |
|---|---|---|
| *G10L 21/003* | (2013.01) | |
| *G10L 21/0364* | (2013.01) | |
| *G10L 15/26* | (2006.01) | |
| *G09B 19/04* | (2006.01) | |
| *G09B 23/28* | (2006.01) | |
| *A61B 5/05* | (2006.01) | |
| *G09B 5/04* | (2006.01) | |
| *G10L 13/02* | (2013.01) | |
| *G10L 21/06* | (2013.01) | |
| *A61B 5/16* | (2006.01) | |
| *G10L 13/00* | (2006.01) | |

(52) U.S. Cl.
CPC ............. *G09B 19/04* (2013.01); *G09B 23/28* (2013.01); *G10L 13/02* (2013.01); *G10L 15/26* (2013.01); *G10L 21/003* (2013.01); *G10L 21/0364* (2013.01); *A61B 5/168* (2013.01); *G10L 13/00* (2013.01); *G10L 2021/065* (2013.01)

(58) Field of Classification Search
CPC . A61B 5/4803; G10L 21/003; G10L 21/0364; G10L 15/26; G10L 2021/065; G10L 13/00; G10L 13/02

USPC .............................................................. 704/9
See application file for complete search history.

(56) References Cited

U.S. PATENT DOCUMENTS

| | | | | |
|---|---|---|---|---|
| 8,949,732 | B2* | 2/2015 | Yodo | G06F 3/04847 |
| | | | | 715/777 |
| 9,072,478 | B1* | 7/2015 | Feerst | G09B 7/02 |
| 2006/0215845 | A1 | 9/2006 | Burleigh et al. | |
| 2007/0105073 | A1* | 5/2007 | Kullok | G09B 19/06 |
| | | | | 434/169 |
| 2008/0044034 | A1* | 2/2008 | Hou | H04R 25/70 |
| | | | | 381/60 |
| 2010/0298304 | A1* | 11/2010 | Page | A61K 31/403 |
| | | | | 514/220 |
| 2012/0021390 | A1* | 1/2012 | Dodd | G09B 19/04 |
| | | | | 434/185 |
| 2012/0197153 | A1* | 8/2012 | Kraus | A61B 5/16 |
| | | | | 600/545 |
| 2013/0178731 | A1* | 7/2013 | Bosl | A61B 5/04012 |
| | | | | 600/409 |
| 2017/0046973 | A1* | 2/2017 | Kuddo | H04R 25/70 |
| | | | | 381/60 |

FOREIGN PATENT DOCUMENTS

| | | | |
|---|---|---|---|
| WO | 0126420 A2 | 4/2001 | |
| WO | WO-0126420 A2 * | 4/2001 | ............. G10L 21/04 |

OTHER PUBLICATIONS

Written Opinion of the International Searching Authority for International Application No. PCT/US2014/050893 dated Nov. 21, 2014.
Extended European Search Report for European Application No. 14836493.8, dated Mar. 23, 2017, 7 pages.
International Preliminary Report on Patentability issued in related International Application No. PCT/US2014/050803.
Notice of Reasons for Rejection for Japanese Application No. 2016-534814, dated Jul. 31, 2018 with translation, 3 pages.

* cited by examiner

DEVICE FOR ENHANCEMENT OF LANGUAGE PROCESSING IN AUTISM SPECTRUM DISORDERS THROUGH MODIFYING THE AUDITORY STREAM INCLUDING AN ACOUSTIC STIMULUS TO REDUCE AN ACOUSTIC DETAIL CHARACTERISTIC WHILE PRESERVING A LEXICALITY OF THE ACOUSTICS STIMULUS

STATEMENT REGARDING FEDERALLY SPONSORED RESEARCH

This invention was made with government support under Grant Nos. R01DC008871 and R01HD073258 awarded by the National Institutes of Health. The Government has certain rights in the invention.

CROSS REFERENCE TO RELATED APPLICATION

This application is the U.S. national phase entry of International Application No. PCT/US2014/050893, filed Aug. 13, 2014, which claims priority to U.S. Provisional Application Ser. No. 61/865,293 entitled DEVICE FOR ENHANCEMENT OF LANGUAGE PROCESSING IN AUTISM SPECTRUM DISORDERS AND RELATED LANGUAGE IMPAIRMENTS, filed Aug. 13, 2013. The contents of International Application No. PCT/US2014/050893 and U.S. Provisional Application Ser. No. 61/865,293 are incorporated fully herein by reference.

FIELD OF THE INVENTION

The present invention relates to language processing. More particularly, the present invention relates to devices and methods for language processing enhancement for individuals with language impairment disorders based on reduction of acoustic detail in the auditory stream.

BACKGROUND OF THE INVENTION

Autism spectrum disorder (ASD) refers to a set of developmental disorders which are identified in children and continue into adulthood; characteristic symptoms of ASD involve deficits in language and communication, in addition to difficulties with social integration/interaction, and repetitive movements. The prevalence of ASD (e.g., about 1 out of 110 individuals have at least one spectrum disorder), with a large number of ASD children being profoundly impaired in language (e.g., with about 40% without any linguistic behavior).

Some children on the autism spectrum (and possibly related neuropsychiatric disorders such as central auditory processing delay (CAPD)) have a difficulty in "abstracting" or forming perceptual objects from acoustically distinct, but conceptually identical stimuli. An example would include difficulty in the encoding of the same word spoken by different speakers. This difficulty in abstracting has implications for ASD individuals with respect to their systems of word (lexical) processing and representation, including the speed and success of activation of abstract lexical representations.

SUMMARY OF THE INVENTION

The present invention relates to a method of auditory manipulation of an auditory stream for enhancement of language processing in an autism spectrum disorder (ASD) individual. A processor receives the auditory stream, where the auditory stream includes an acoustic stimulus perceptually representing an object. An acoustic manipulation parameter is selected for a predetermined acoustic detail characteristic. The predetermined acoustic detail characteristic is associated with the ASD individual and based on a measured language processing capability of the ASD individual. The processor modifies the auditory stream based on the selected acoustic manipulation parameter. The modification to the auditory stream reduces the predetermined acoustic detail characteristic while preserving a lexicality of the stimulus, such that the reduced acoustic detail characteristic enhances perception of the object by the ASD individual even when the stimulus includes two or more acoustically distinct stimuli each perceptually representing the object. The modified auditory stream is output to the ASD individual via at least one loudspeaker.

The present invention also relates to a device for auditory manipulation of an auditory stream for enhancement of language processing in an autism spectrum disorder (ASD) individual. The device includes an audio input interface, a non-transitory tangible storage device, an acoustic detail manipulation unit and at least one loudspeaker. The audio input interface is configured to receive the auditory stream, where the auditory stream includes an acoustic stimulus perceptually representing an object. The storage device is configured to store acoustic manipulation parameters for a predetermined acoustic detail characteristic. The predetermined acoustic detail characteristic is associated with the ASD individual and based on a measured language processing capability of the ASD individual. The acoustic detail manipulation unit is configured to: select an acoustic manipulation parameter among the stored acoustic manipulation parameters for the predetermined acoustic detail characteristic and modify the auditory stream based on the selected acoustic manipulation parameter. The modification to the auditory stream reduces the predetermined acoustic detail characteristic while preserving a lexicality of the stimulus, such that the reduced acoustic detail characteristic enhances perception of the object by the ASD individual even when the stimulus includes two or more acoustically distinct stimuli each perceptually representing the object. The at least one loudspeaker is configured to output the modified auditory stream to the ASD individual.

BRIEF DESCRIPTION OF THE DRAWINGS

The invention may be understood from the following detailed description when read in connection with the accompanying drawings. It is emphasized that, according to common practice, various features/elements of the drawings may not be drawn to scale. On the contrary, the dimensions of the various features/elements may be arbitrarily expanded or reduced for clarity. Moreover, in the drawings, common numerical references are used to represent like features/elements. Included in the drawings are the following figures.

DETAILED DESCRIPTION OF THE INVENTION

Figure 1:
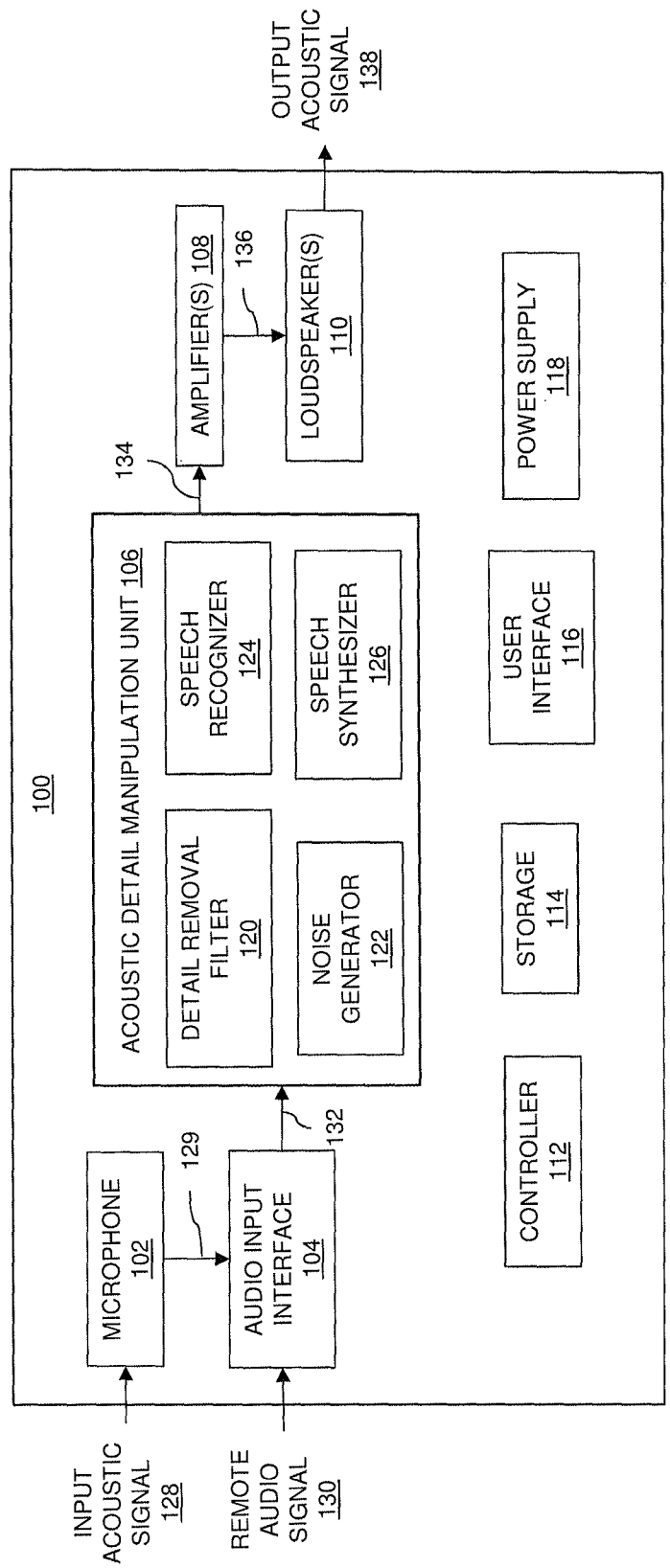
FIG. 1 is a functional block diagram of an example auditory manipulation device for language processing enhancement, according to an embodiment of the present invention.

As discussed above, ASD individuals have difficulty abstracting perceptual objects from acoustically distinct but conceptually identical stimuli. This difficulty may be caused by impairment in the basic building blocks of language function, by the creation of redundant representations of the same "object", colored by too much attention to irrelevant acoustic detail.

Evidence for such failure may be seen in electrophysiologic responses (e.g., recorded by magnetoencephalography (MEG), a type of functional brainwave mapping which allows depiction of brain function in space and time) indicating lack of "clustering" of responses around perceptual objects, a heightened sensitivity to acoustic (but not linguistic) differences and a general delay processing auditory input (secondary to exerting too much effort processing minor acoustic differences). Priming effects (both electrophysiologically and behaviorally) would also indicate heightened attention to "irrelevant" details, precluding perceptual object formation.

In general, spoken words may contain too much sound information; that is, more information than is needed to "decode" the intended "object" or meaning. Sometimes, that extra detail helps in higher order distinctions (e.g., was it a male or a female speaker . . . ? were they angry . . . ?) and sometimes it just fluctuates (speaker to speaker, or even day to day). Typical development allows a tolerance to such "minor" acoustic or sound differences and permits clustering of different "sound" events into the same "word". By over-reliance on sound details, or by inability to cluster, or both, the ASD brain may fail to tolerate sound differences that are essentially irrelevant to meaning extraction.

It may be appreciated that "relevance" may be in the eye (ear) of the beholder—generally concepts of "irrelevance" are referred to herein as factors not necessary to relay or impart object recognition, representation and ultimately meaning.

Every sound, even a speech sound like a word, contains acoustic features or details. These include pitch (frequency content), harmonics, richness, etc. These are physical and can be measured directly (or synthesized by a computer, for example). In speech they might reflect speaker (male: low pitch, female: high pitch), intonation (angry/sad) or urgency (speed of transients etc.); or they might just be the result of fluctuations in the speech apparatus. What matters is that the same "word" such as "cat" could be uttered by different speakers, with different intonations or different urgency (or simply on different occasions) and each utterance would have slight-moderate "acoustic differences". However, to a "normal ear/brain", all would be perceived as a single "object", namely a cat. A linguistic difference might be embodied in a special case of an acoustic difference, where the difference is sufficient to transform the perceived object from e.g. "cat" to "cap", with associated different meaning. The ASD brain may fail to appropriately "cluster" across acoustic differences and thus hears different versions of "cat" as multiple different objects (and thus may not arrive at the intended meaning either as quickly or accurately, in essence because of giving too much weight or significance to "acoustic differences" that are irrelevant to arriving at an appropriate representation or meaning).

Typical electrophysiologic responses to words (as opposed to non-words like "blik", for example) are associated with spectrotemporal features (specifically decreased oscillatory power in the 5-15 Hz band, a fraction of a second after the word is recognized). Responses in ASD may be delayed or attenuated. This may be scanned and detected using MEG.

Lexical processing in typically developing (TD) individuals involves both abstract and episodic components. Every single time a word (e.g., cat) is heard, it has physically distinct properties: individual speaker voice, speaker gender, differences in prosody and volume, etc., making every spoken word a unique event. The TD brain is able to abstract from all of these distinct acoustic objects ($CAT_1 \ldots CAT_n$) a single lexical representation of "cat." The TD brain does this by factoring out irrelevant phonetic detail, and working with a phonological representation /kaet/ that serves as the basis for lexical representation. At the same time, the TD brain might also be sensitive to some episodic properties of words, so that some aspects of individual instances of heard words (e.g., information about speaker, or speech rate, or phonetics) are represented in memory as well, where they have some effect in linguistic processing. The abstract component tends to be more important for linguistic representation and processing of words, because, when cat is heard, the lexical-semantic (and other, e.g., syntactic) properties of this lexical item are activated. For ASD, a population with a general problem with abstraction, and over-attention to low-level detail, the episodic aspect of lexical processing predominates over or compensates for the abstract system, with consequences for the linguistic system.

Recognizing an auditorily presented word involves a number of distinct computations in the brain. These computations include: converting the acoustic signal into phonological representations (linguistic representations of sound); matching the incrementally derived sound representations with words in the hearer's brain (e.g., after hearing the first two segments of cat, [kae], the brain has partially activated cat, cap, cab, etc.); and selecting one of the activated candidates as the winner, when enough of the word's sound form is known so that this can be done. For example, after the final segment [t] of cat is heard, the word cat is fully activated in the hearer's brain. This view of lexical access involves three key notions that play a role in our investigation of the ASD brain. Lexical access involves the onset of lexical search/activation (lex-search), a recognition point at which the brain identifies the target word (recog-point) and a uniqueness point in the acoustic signal of the word at which that word becomes uniquely identifiable, such as the final [t] of cat).

Figure 4A:
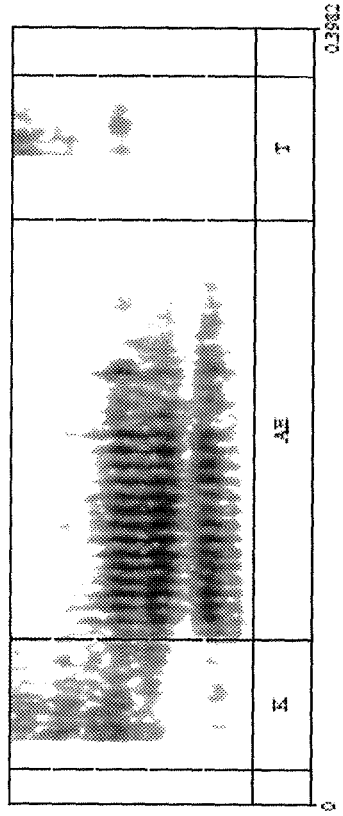
FIG. 4A is a spectrogram illustrating an example uniqueness point of the word "cat," according to an embodiment of the present invention.
Figure 4B:
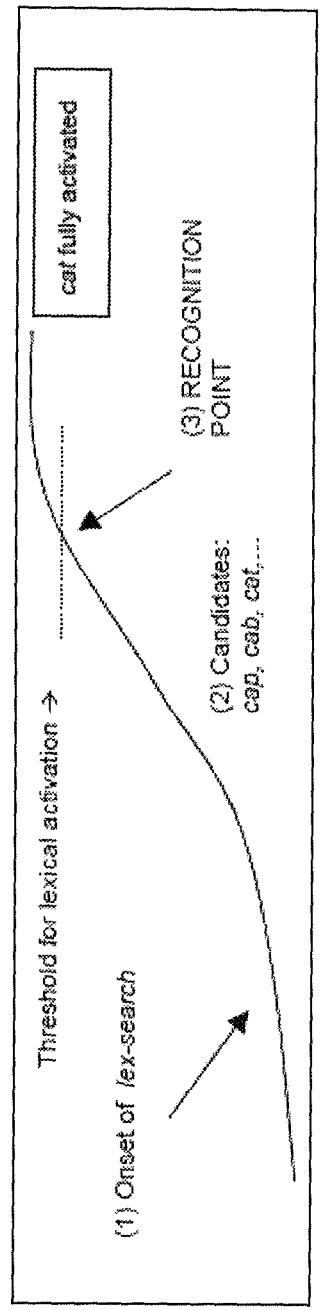
FIG. 4B is a graph of an example activation of the word "cat" as a function of time, according to an embodiment of the present invention.

FIGS. 4A and 4B illustrate the lexical access described above for the word "cat." FIG. 4A is an example spectrogram of a speech signal including the word "cat," and FIG. 4B is a graph of an example lexical access of the word "cat" as a function of time. FIG. 4A is time-locked with the lexical brain activity shown in FIG. 4B. As shown in FIGS. 4A and 4B, the uniqueness point of cat is determined by the final consonant sound [t]. The lexical system (in FIG. 4B) is able to raise the processed word above the threshold only after the uniqueness point has been processed.

FIG. 4B shows increasing activation (schematized on the y-axis) of lexical access mechanisms in the brain over time. The incoming speech signal triggers increased auditory processing. As the acoustic signal is converted into phonological representations, activation devoted to the lex-search increases, with onset immediately after the acoustic signal is recognized as speech (region 1). The lexical search produces a number of candidate lexical items compatible with incrementally-processed input (region 2). When the uniqueness point of the word arrives, the lexical system raises the activation of the winning candidate cat above threshold (region 3), the recognition point. The word cat is then fully activated.

The ASD brain is delayed with respect to early auditory responses, which results in a slower onset of auditory processing. Thus, the lex-search component is delayed and/or less robust. The ASD brain's inability to abstract/concentrate on relevant phonetic detail may also make it unable to recognize different phonetic tokens of the same phonological sequence to be recognized as the same sequence. An immediate consequence is that it is not possible to produce candidates for the lex-search, and to reach a threshold for a single word (recognition-point) with the speed and accuracy of TD individuals.

A priming effect (both behaviorally and in terms of quantitative features of the MEG recoding, described above) can be observed for example by repetition. For example, "cat" after "cat" is processed faster and has muted electrophysiologic responses compared to "cat" after "truck". Of note, "cat" after "dog" is a bit of a middle ground—because of their relatedness—called "semantic priming". However, if tokens of "cat" are perceived as distinct objects because of too much emphasis on "irrelevant" "acoustic details", then priming effects could be lost in ASD. In fact, the degree of priming effect attenuation might indeed index the degree of perceptual clustering deficit, and ultimately language impairment.

Irrelevant acoustic details may be generally defined as "acoustic differences" that should typically detract from the appreciation of the word (and its representation, or meaning) but that might cause separate classification in the ASD brain which "cannot see (hear) the forest for the trees". A simple example would be pitch (reflecting speaker, but not changing meaning).

Aspects of the present invention relate to acoustic manipulation of the auditory stream (e.g., such as via a hearing aid-type device), to improve perceptual object formation from acoustically distinct, but conceptually identical stimuli. Example methods and devices relate to auditory manipulation of an auditory stream for enhancement of language processing in an autism spectrum disorder (ASD) individual. The auditory stream includes an acoustic stimulus perceptually representing an object. An acoustic manipulation parameter may be selected for a predetermined acoustic detail characteristic. The predetermined acoustic detail characteristic is associated with the ASD individual and is based on a measured language processing capability of the ASD individual. An acoustic detail manipulation unit may modify the auditory stream based on the selected acoustic manipulation parameter. The modification to the auditory stream reduces the predetermined acoustic detail characteristic while preserving a lexicality of the stimulus, such that the reduced acoustic detail characteristic enhances perception of the object by the ASD individual even when the stimulus includes two or more acoustically distinct stimuli each perceptually representing the object. The modified auditory stream may be output to the ASD individual via at least one loudspeaker.

Referring to FIG. 1, a functional block diagram of an example auditory manipulation device, designated generally as device 100, is shown. Device 100 may manipulate auditory stream 132, by reducing predetermined acoustic detail characteristics of auditory stream 132. The modified audio signal 134 (with reduced acoustic detail) may enhance language processing for ASD individuals, by improving perceptual object formation from acoustically distinct but conceptually identical stimuli). The predetermined acoustic detail characteristics (also referred to herein as predetermined characteristics) to be reduced may be associated with a language processing capability of a user of device 100. The predetermined characteristics (and device 100 in general) may be calibrated based on the user's language processing capability (described further below with respect to FIG. 2).

Device 100 may include microphone 102, audio input interface 104, acoustic detail manipulation unit 106, amplifier(s) 108, loudspeaker(s) 110, controller 112, storage 114, user interface 116 and power supply 118. Microphone 102, audio input interface 104, acoustic detail manipulation unit 106, amplifier(s) 108, loudspeaker(s) 110, controller 112, storage 114, user interface 116 and power supply 118 may be coupled together via a data and control bus (not shown). Power supply 118 may include any suitable power supply (such as a battery) capable of powering components of device 100. Although not shown, device 100 may include a data communication interface, for wired or wireless communication with a remote device. Although not shown, device 100 may be coupled to a remote location, for example via a global network (i.e., the Internet).

In some examples, device 100 may be configured as a hearing device, including, without being limited to, a behind-the-ear (BTE) type device, an in-the ear (ITE) type device, an in-the-canal (ITC) device or as a wearable hearing device. Loudspeaker(s) 110 may be configured to be positioned in the user's ear(s) (such as in an earpiece). In some examples, device 100 is a monaural device, and includes one loudspeaker 110 (and one corresponding amplifier 108). In other examples, device 100 is a binaural device, and includes two loudspeakers 110 (and two corresponding amplifiers 108). In some examples, device 100 may include components (such as microphone 102, audio input interface 104, acoustic detail manipulation unit 106, amplifier 108, controller 112, storage 114, user interface 116 and power supply 118) that may be configured in one housing unit. The housing unit may be worn on any part of the user's body (for example, on the user's belt, in a pocket, as a pendent around the user's neck, on a wristband on the user's wrist, etc.). Loudspeaker(s) 110 may be formed in an earpiece(s) positioned in the user's ear(s) (such as at the entrance to the ear canal or in the ear canal) and coupled to the housing unit.

Microphone 102 is configured to receive an input acoustic signal 128 from the ambient acoustic environment, such as from an individual proximate to microphone 102. Microphone 102 may include any suitable transducer capable of converting the input acoustic signal 128 to an (electronic) audio signal 129.

In some examples, audio input interface 104 is configured to receive remote audio signal 130 (an electronic signal) from a remote device such as a phone (including a mobile phone), a computer, a television, an audio playback device, a video playback device (having audio capability) or any device capable of providing remote audio signal 130. The remote device (not shown) may be wired or wirelessly coupled to audio input interface 104. Audio input interface 104 may also include an analog-to-digital converter (ADC) for converting audio signal 129 (from microphone 102) to a digital signal. In general, audio input interface receives audio signal 129 and/or remote audio signal 130 and converts these signals to an auditory stream 132. Audio input interface 104 may include any hardware and/or software components to receive and/or modify audio signal 129 (and/or audio signal 130) to form auditory stream 132 in a format suitable for processing by acoustic detail manipulation unit 106.

Acoustic detail manipulation unit 106 is configured to receive auditory stream 132 and to provide a modified audio signal 134. Modified audio signal 134 may be acoustically manipulated by one or more components of acoustic detail manipulation unit 106, to reduce one or more predetermined acoustic detail characteristic(s) of auditory stream 132, based on the language processing capability of the user. Acoustic detail manipulation unit 106 may include one or more of: a detail removal filter 120, a noise generator 122, a speech recognizer 124 and a speech synthesizer 126. In some examples, acoustic detail manipulation unit 106 may include one component (such as detail removal filter 120 or noise generator 122). In other examples, acoustic detail manipulation unit 106 may include only speech recognizer 124 and speech synthesizer 126. The components to be included in acoustic detail manipulation unit 106 may be selected upon calibration of device 100 for the user (described further below with respect to FIG. 2). Acoustic detail manipulation unit 106 may include any suitable software and/or hardware components to manipulate auditory stream 132 to reduce the predetermined acoustic detail characteristic(s). The predetermined acoustic detail characteristic(s) may be associated with parameters selected (and stored in storage 114) for detail removal filter 120, noise generator 122, speech recognizer 124 and/or speech synthesizer 126. The modification of auditory stream 132, in general, reduces the predetermined acoustic detail characteristic(s) while preserving a lexicality of the degraded stimulus (i.e., the modified stimulus still sounds like a word).

Detail removal filter 120 may be configured to receive auditory stream 132, and to filter or smooth auditory stream 132 such that all (or a suitable portion of) "extraneous" detail is removed. The filtered signal from detail removal filter 120 may form modified audio signal 134. Detail removal filter 120 may include a filter having a predetermined filter characteristic (such as a low-pass filter, a band-pass filter, a high-pass filter, etc.). For example, a majority of spectral energy in human speech is in the range of 100 Hz to 1 kHz. Accordingly, in an example embodiment, a band-pass filter which passes frequencies in the 20 Hz to 20 kHz range may be used.

The word "extraneous" relates to details that are not relevant (and may indeed be distracting to ASD) for the purposes of identifying the "object" which the uttered sound (word) represents (e.g., intonation, frequency dynamics, etc.). An example filtering approach may remove high frequency sibilants, etc., that might convey acoustic "attack" (onset abruptness) or intonation, but that should prevent definition of a unique representation. Such an approach is similar to a low-pass filter which filters speech while maintaining the essence of the conversation.

Filter parameters (such as the cutoff frequency, the center frequency, the filter type) of device 100 may be tuned to the individual user. As such, a calibration may be performed on device 100 to adjust the filter parameters to the user, prior to its use. In addition, the calibration may also provide a quantitative index of therapeutic intervention. Filter parameters and the quantitative index may be further adjusted over time (e.g., the index may be reduced indicating a successful progress).

As another example, detail removal filter 120 may be configured to receive auditory stream 132 having a first sampling rate, and to sub-sample auditory stream 132 with a predetermined second sampling rate, such that the second sampling rate (of filter 120) is less than the first sampling rate (of auditory stream 132). The predetermined second sampling rate may be selected to reduce the predetermined acoustic detail characteristics, which may be calibrated to the user. The sub-sampled signal from detail removal filter 120 may form modified audio signal 134.

Noise generator 122 may be configured to receive auditory stream 132 and apply (i.e., add) noise having a predetermined noise characteristic to auditory stream 132. The predetermined noise characteristic may be selected to saturate acoustic details of auditory stream 132, such that the listener focuses only on the core auditory input. The noise-added signal from noise generator 122 may form modified audio signal 134.

For example, white noise (i.e., having a uniform broad band power spectral density) or colored noise (e.g., pink noise having a low frequency emphasis, with a power spectral density inversely proportional to frequency) may be added to auditory stream 132. White noise may be approximated, for example, by a pseudorandom noise generator. While the noise generally reduces sensitivity (commonly thought of as "intelligibility"), the noise may mask the extraneous features of auditory stream 132, thus allowing the essence of the conversation to be appreciated (to force a desired clustering).

The predetermined noise characteristic may include a spectral distribution (such as white noise or pink noise) and/or an amplitude of each component of the spectral distribution. The predetermined noise characteristic may be tailored to the individual according to their hearing (audiology/audiometric testing), brain responses or through theoretical personalization. Similar to the predetermined filter parameters of detail removal filter 120, the predetermined noise characteristic may also be monitored and/or adjusted over time.

Speech recognizer 124 may be configured to receive and apply speech recognition processing to auditory stream 132, to form a text representation of auditory stream 132. Speech synthesizer 126 may be configured to receive the recognized speech (from speech recognizer 124) and convert the recognized speech to a single speech production voice via speech synthesis processing. The speech recognition and speech synthesis processing by respective speech recognizer 124 and speech synthesizer 126 may be performed in real time. The speech production voice produced by speech synthesizer 126 may have predetermined speech characteristics that are tuned (i.e., calibrated) to the individual. Thus, auditory input from several different speakers may be recognized as a same perceptual object (by speech recognition) and converted to a single speech production voice (having the same predetermined speech characteristics regardless of the acoustic characteristics of the speakers). The speech production voice from speech synthesizer 126 may form modified audio signal 134.

Speech recognizer 124 may use any suitable speech recognition technique (such as used by automated dictation systems) to recognize multiple voices (i.e., voices from different individuals) and distil the essence of each voice into text. Example speech recognition techniques include, without being limited to, acoustic modeling and/or language modeling techniques, including Hidden Markov Models (HMMs), and neural networks. Speech synthesizer 126 may interpret text (from speech recognizer 124) and reproduce human speech (but always with the same pitch, intonation etc., according to the predetermined speech characteristics). Thus, speech synthesizer 126 does not introduce variability in acoustic details associated with a particular word. Accordingly, reproducible word sounds may be produced by loudspeaker 110 in response to variable word sounds captured by microphone 102 or received from a remote device.

Similar to the filter parameters of detail removal filter 120, the predetermined speech characteristics of speech synthesizer 126 may be calibrated to the individual user. A quantitative index of therapeutic intervention may be determined during calibration. Similar to the filter parameters, the predetermined speech characteristics and quantitative index may also be monitored/adjusted over time (e.g., the index may be reduced indicating a successful progress).

In some examples, both detail removal filtering and noise generation via respective detail removal filter 120 and noise generator 122 may be applied to auditory stream 132. In some examples, the speech synthesized signal (from speech synthesizer 126) may be applied to detail removal filter 120 and/or noise generator 122, for further acoustic detail removal. The selection of components of acoustic detail manipulation unit 106 may be tailored to the user's language processing capability.

Amplifier(s) 108 may be configured to receive and amplify modified audio signal 134 from acoustic detail manipulation unit 106, to form amplified signal 136. Amplifier(s) 108 may include any hardware and/or software components to amplify modified audio signal 134, based on a predetermined gain stored in storage 114 and/or a user setting received via user interface 116 (such as a volume adjustment). For a binaural device, each amplifier 108 may be calibrated with a predetermined gain for the respective ear, such as based on a hearing (i.e., auditory) test. Thus, if the user has a hearing loss in one ear or different hearing capabilities in each ear, the predetermined gain for each amplifier 108 may be different. In some examples, amplifier(s) 108 may also apply different gains in different frequencies (of a frequency band) to compensate for hearing loss in different frequencies. The frequency-dependent gains applied by amplifiers 108 (for a binaural device) may be the same or different, depending on the hearing capability of each of the user's ears. In some examples, amplifier(s) 108 (or acoustic detail manipulation unit 106) may include a digital-to-analog converter (DAC) for converting digital signal 134 to an analog signal 136.

Loudspeaker(s) 110 is capable of receiving modified signal 134 from acoustic detail manipulation unit 106 and/or amplified signal 136 from amplifier(s) 108. Loudspeaker(s) 110 may include any suitable transducer capable of converting the modified signal 134 (or amplified signal 136) into output acoustic signal 138, such that output acoustic signal 138 is provided to the user's ear(s).

Controller 112 may be coupled to one or more of: microphone 102, audio input interface 104, acoustic detail manipulation unit 106, amplifier(s) 108, loudspeaker(s) 110, storage 114, user interface 116 and power supply 118, to control the capture of auditory stream 132 (via microphone 102 or directly via audio input interface 104), control auditory manipulation of auditory stream 132 and/or to control output of the modified auditory stream 134 (via amplifier(s) 108 and loudspeaker(s) 110). Controller 112 may include, for example, a conventional digital signal processor, a logic circuit or a microprocessor. It is understood that one or more functions of acoustic detail manipulation unit 106 may be performed by controller 112. It will be understood by one of skill in the art from the description herein that one or more of the functions of acoustic detail manipulation unit 106, audio input interface 104, and amplifier(s) 108 may be implemented in software and may be performed by controller 112.

Storage 114 may be configured to store parameters for at least one of audio input interface 104, detail removal filter 120, noise generator 122, speech recognizer 124 and speech synthesizer 126 (i.e., predetermined acoustic detail characteristics of the user). Storage 114 may also store parameters for at least one of audio input interface 104 and amplifier(s) 108. Storage 114 may also store one or more predetermined sound stimuli, for calibration of device 100 (including the user's predetermined acoustic detail characteristics). Storage 114 may also store any user settings for device 100 (such as volume control). Storage 114 may be a memory, a magnetic disk, a database or essentially any local or remote non-transitory, tangible device capable of storing data.

User interface 116 may include any suitable interface for capturing audio stream 132, outputting modified audio signal 134, indicating storage, calibration of device 100 and/or display of quantities. User interface 116 may include any suitable user interface capable of providing parameters associated with one or more of audio input interface 104, acoustic detail manipulation unit 106 and amplifier(s) 108. User interface 116 may further include an input device such as a keypad or touchpad for entering information. User interface 116 may further include a display device for presenting information to the user.

Suitable embodiments of microphone 102, audio input interface 104, acoustic detail manipulation unit 106, amplifier(s) 108, loudspeaker(s) 110, controller 112, storage 114, user interface 116 and power supply 118 may be understood by the skilled person from the description herein.

Figure 2:
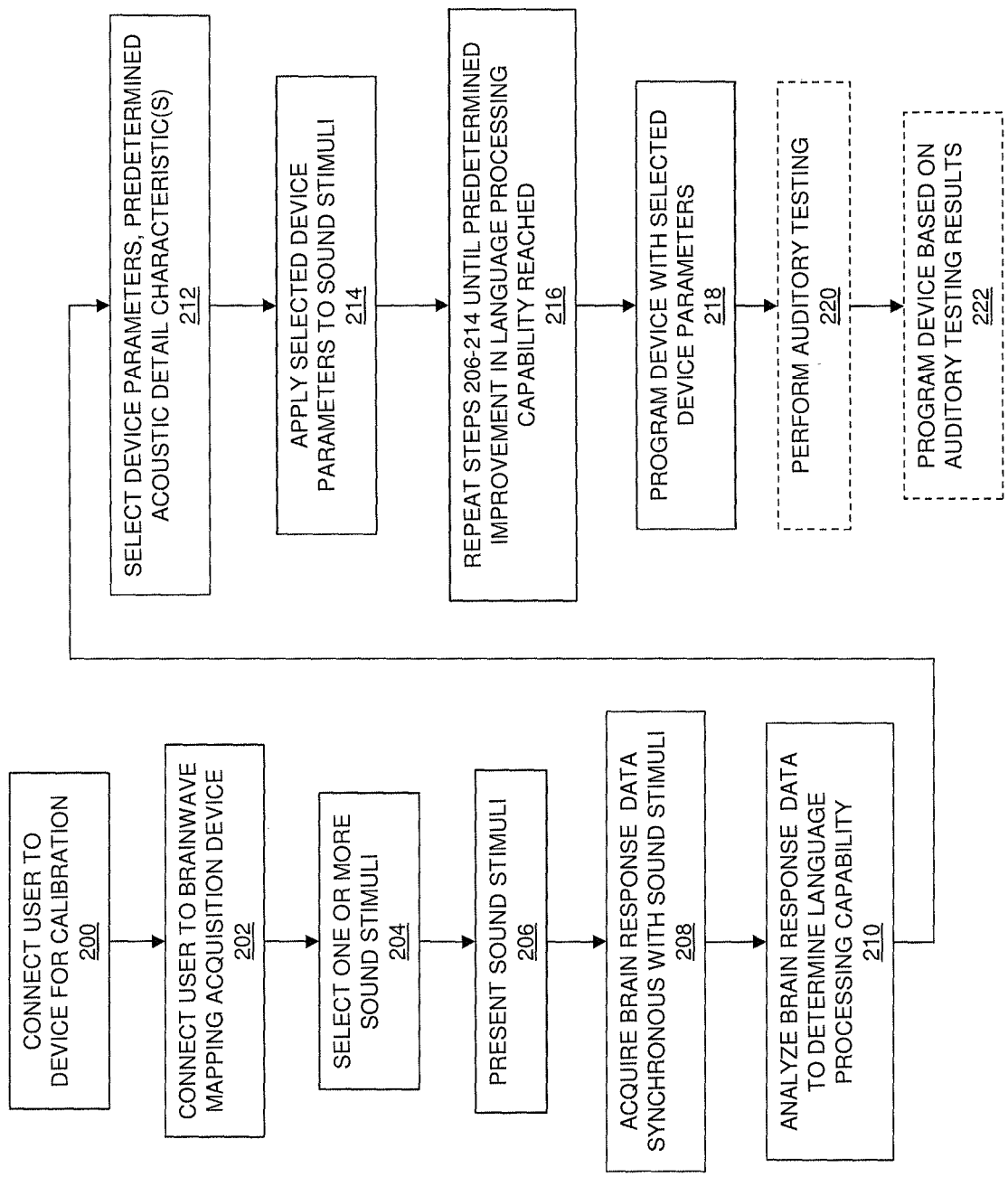
FIG. 2 is a flowchart of an example method for calibration of an auditory manipulation device, according to an embodiment of the present invention.

Referring next to FIG. 2, a flowchart of an example method for calibration of auditory manipulation device is shown. The example method may be used to calibrate parameters of device 200 associated with a user of device 100, based on the language processing capability of the user. At step 200, a user is connected to device 100 (FIG. 1), for calibration of parameters of device 100. At step 202, the user is connected to a brainwave mapping acquisition device, such as an MEG acquisition device, in order to acquire brain responses (such as neuromagnetic data) during the calibration.

At step 204, one or more sound stimuli are selected, to determine the user's language processing capability.

At step 206, the sound stimuli are presented to the user via loudspeaker(s) 110 (FIG. 1) of device 100. At step 208, brain response data is acquired (via the brainwave mapping acquisition device) simultaneously with the presented sound stimuli (step 206). At step 210, the brain response data is analyzed to determine the language processing capability of the user.

At step 212, acoustic detail characteristic(s) to be reduced are determined, and parameters for device 100 are selected (based on the determined characteristic(s), based on the processing capability of the user (determined in step 210). The parameters are selected for detail removal filter 120, noise generator 122, speech recognizer 124 and/or speech synthesizer 126, to reduce a predetermined acoustic detail characteristic(s) of the sound stimuli. The selected parameters may be used for auditory manipulation of input audio; by filtering, the addition of noise and/or use of a single speech production voice with predetermined speech characteristics.

At step 214, the selected parameters (step 212) are applied to the sound stimuli (selected in step 204) to manipulate the sound stimuli, in order enhance the user's language processing capability. At step 216, steps 206-214 are repeated with the manipulated sound stimuli (step 214), and the parameters of device 100 are adjusted until a predetermined improvement in language processing capability of the user is determined. For example, the uniqueness point and recognition point during a lexical access. A uniqueness point and/or recognition point that occurs earlier in time (See FIG. 4B) may indicate that the manipulation improves the language processing of the individual. At step 218, device 100 is programmed with the parameters determined in step 216.

At optional step 220, audiometric testing may be performed on the user. At optional step 222, device 100 may be further programmed based on the audiometric testing results of step 220. For example, one or more gain parameters of amplifier(s) 108 may be selected based on the audiometric testing results. In another example, calibration of device 100 may also be based on theoretical personalization.

Figure 3B:
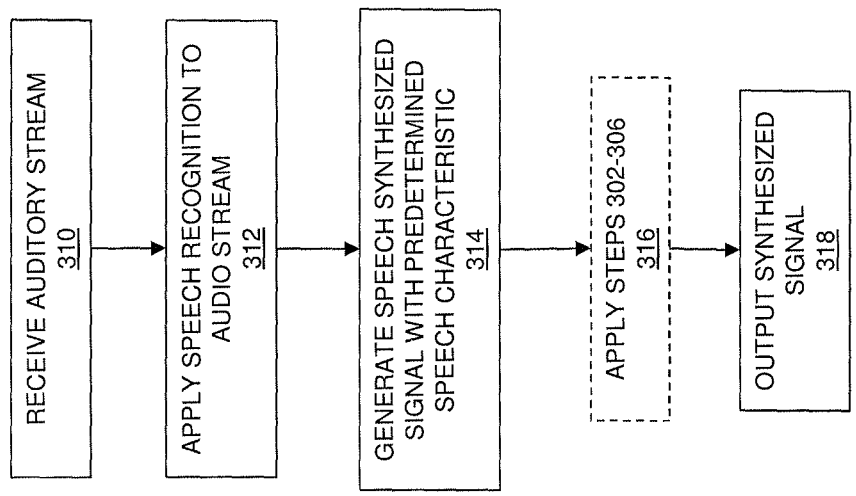
FIG. 3B is a flowchart diagram of an example method of auditory manipulation for enhancement of language processing, according to another embodiment of the present invention.
Figure 3A:
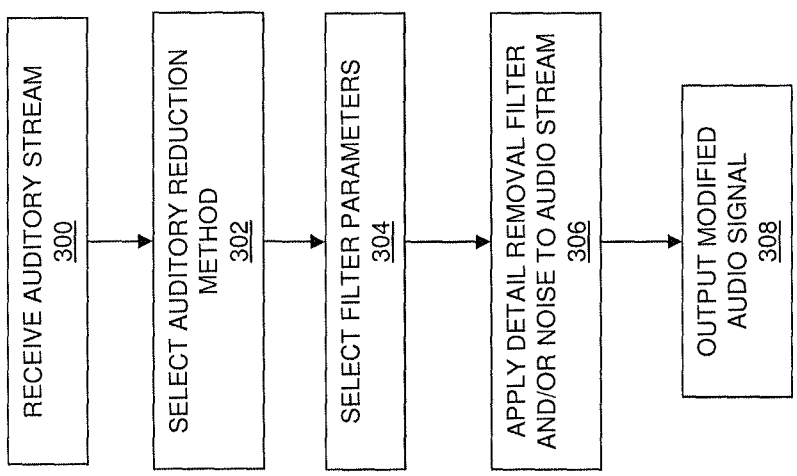
FIG. 3A is a flowchart diagram of an example method of auditory manipulation for enhancement of language processing, according to an embodiment of the present invention.

FIGS. 3A and 3B illustrate example methods of auditory manipulation for enhancement of language processing, via acoustic detail manipulation unit 106 (FIG. 1). In particular, FIG. 3A is a flowchart diagram of an example auditory manipulation of auditory stream 132 (FIG. 1) via detail reduction filtering and/or noise addition; and FIG. 3B is a flowchart diagram of an example auditory manipulation of auditory stream 132 via speech recognition and speech synthesis.

Referring to FIG. 3A, at step 300, auditory stream 132 is received by acoustic detail manipulation unit 106. At step 302, an auditory reduction method is selected, for example, via controller 112. For example, controller 112 may select detail removal filtering via filter 120 and/or noise addition filtering via noise generator 122. At step 304, parameters are selected for detail removal filter 120 and/or noise generator 122, for example, via controller 112 using filter/noise parameters stored in storage 114.

At step 306, detail removal filtering and/or noise addition is applied to auditory stream 132, via respective detail removal filter 120 and noise generator 122. At step 308, modified signal 134 (after filtering and/or noise addition) is output from acoustic detail manipulation unit 106. Although not shown in FIG. 3A, modified signal 134 may also be converted to an analog signal and/or may be amplified by amplifier(s) 108 before being transduced to output acoustic signal(s) 138 by loudspeaker(s) 110.

Referring to FIG. 3B, at step 310, auditory stream 132 is received by acoustic detail manipulation unit 106. At step 312, speech recognition is applied to auditory stream 132, via speech recognizer 124. At step 314, speech synthesis is applied to the recognition result (step 312), via speech synthesizer 126. Speech synthesizer 126 may select a speech production voice with predetermined speech characteristics. For example, the predetermined speech characteristics may be selected by controller 112, using predetermined speech characteristics stored in storage 114.

At optional step 316, steps 302-306 may be applied, to apply detail removal filtering and/or the addition of noise to the speech production voice (synthesized in step 314). At step 318, modified signal 134 (after speech synthesis in step 314 or after filtering/noise addition in optional step 316) is output from acoustic detail manipulation unit 106. Similar to FIG. 3A, modified signal 134 may also be converted to an analog signal and/or may be amplified by amplifier(s) 108 before being transduced to output acoustic signal(s) by loudspeaker(s) 110.

Auditory manipulation according to the present invention may be used to eliminate irrelevant acoustic detail, thus leading to stronger abstract (e.g., word, etc.) representations that may be accessed more rapidly in real time. Thus, exemplary device 100 may reduce (or substantially eliminate) irrelevant detail from acoustically presented words. This may aide the ASD brain to identify words with increased speed and accuracy, leading to more robust lexical representations for the ASD individual, with an overall positive effect on language and communication. Such approaches may be evaluated by similar electrophysiologic and behavioral assessments as described herein (e.g., MEG clustering, mismatch field and auditory processing latencies, as well as behavioral assays of repetition priming). Improvement in the categorization and abstraction by acoustic manipulation of stimuli may improve the user's lexical system, by making it easier for the ASD brain to recognize words. These processing benefits may extend beyond lexical access into more abstract parts of language (such as decomposition of morphologically complex words, syntactic processing and semantics).

Although the invention has been described in terms of devices and methods for enhancing language processing in individuals with ASD, it is contemplated that one or more steps and/or components may be implemented in software for use with microprocessors/general purpose computers (not shown). In this embodiment, one or more of the functions of the various components and/or steps described above may be implemented in software that controls a computer. The software may be embodied in non-transitory tangible computer readable media (such as, by way of non-limiting example, a magnetic disk, optical disk, flash memory, hard drive, etc.) for execution by the computer.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method of auditory manipulation of an auditory stream of target speech for enhancement of language processing in an autism spectrum disorder (ASD) individual, the ASD individual having been identified as having ASD based on a measured language processing capability that is determined based on the ASD individual's brainwave response to test speech, the measured language processing capability being insufficient to abstract perceptual objects from acoustically distinct but conceptually identical words, the method comprising:

receiving, by a processor, the auditory stream of the target speech perceptually representing an object;

selecting an acoustic manipulation parameter for a predetermined acoustic detail characteristic associated with the ASD individual, the acoustic manipulation parameter computed based on the measured language processing capability of the ASD individual in response to the test speech;

modifying, by the processor, the auditory stream of the target speech based on the selected acoustic manipulation parameter, to reduce the predetermined acoustic detail characteristic of the target speech while preserving a lexicality of the target speech, such that the reduced acoustic detail characteristic enhances perception of the object by the ASD individual when the target speech includes two or more acoustically distinct words each perceptually representing the object; and outputting the modified auditory stream of the target speech to the ASD individual via at least one loudspeaker.

2. The method of claim 1, the method further including: capturing the auditory stream via a microphone proximate to the ASD individual.

3. The method of claim 1, the method further including: receiving the auditory stream from a remote device coupled to the processor, the remote device including at least one of a phone, a computer, a television, and a playback device having an audio capability.

4. The method of claim 1, wherein the step of modifying the auditory stream includes applying a filter to the auditory stream to reduce the predetermined acoustic detail characteristic, the filter having a predetermined filter characteristic based on the selected acoustic manipulation parameter.

5. The method of claim 4, wherein the predetermined filter characteristic includes at least one of a low-pass filter, a band-pass filter and a high-pass filter.

6. The method of claim 1, wherein the step of modifying the auditory stream includes sub-sampling the auditory stream at a predetermined sampling rate to reduce the predetermined acoustic detail characteristic, the predetermined sampling rate based on the selected acoustic manipulation parameter.

7. The method of claim 1, wherein the step of modifying the auditory stream includes adding noise to the auditory stream to reduce the predetermined acoustic detail characteristic, the noise having a predetermined noise characteristic based on the selected acoustic manipulation parameter.

8. The method of claim 1, wherein the step of modifying the auditory stream includes:
performing speech recognition on the auditory stream to form a text representation of the audio stream; and
converting the text representation of the auditory stream to a speech production voice via speech synthesis processing, the speech production voice having a predetermined speech characteristic based on the selected acoustic manipulation parameter.

9. The method of claim 1, the method including, prior to receiving the auditory stream:
presenting at least one predetermined stimulus to the ASD individual via the at least one loudspeaker;
acquiring one or more brain responses from the ASD individual synchronous with the presented at least one predetermined stimulus;
determining the measured language processing capability of the ASD individual based on the acquired one or more brain responses; and
determining the predetermined acoustic detail characteristic to be reduced based on the measured language processing capability.

10. The method of claim 9, wherein the one or more brain responses are acquired from a magnetoencephalography (MEG) acquisition device.

11. The method of claim 1, wherein the predetermined acoustic detail characteristic includes at least one of a pitch, a harmonic, an intonation, a transient sound, a sibilant sound or frequency dynamics of the target speech.

12. A device for auditory manipulation of an auditory stream of target speech for enhancement of language processing in an autism spectrum disorder (ASD) individual, the ASD individual having been identified as having ASD based on a measured language processing capability that is determined based on the ASD individual's brainwave response to test speech, the measured language processing capability being insufficient to abstract perceptual objects from acoustically distinct but conceptually identical words, the device comprising:
an audio input interface configured to receive the auditory stream of the target speech perceptually representing an object;
a non-transitory, tangible storage device configured to store acoustic manipulation parameters for a predetermined acoustic detail characteristic associated with the ASD individual, the acoustic parameter computed based on the measured language processing capability of the ASD individual in response to the test speech;
an acoustic detail manipulation unit configured to:
select an acoustic manipulation parameter among the stored acoustic manipulation parameters for the predetermined acoustic detail characteristic, and
modify the auditory stream of the target speech based on the selected acoustic manipulation parameter, to reduce the predetermined acoustic detail characteristic of the target speech while preserving a lexicality of the target speech, such that the reduced acoustic detail characteristic enhances perception of the object by the ASD individual when the stimulus target speech includes two or more acoustically distinct words each perceptually representing the object; and
at least one loudspeaker configured to output the modified auditory stream of the target speech to the ASD individual.

13. The device of claim 12, wherein the acoustic detail manipulation unit includes a filter configured to filter the auditory stream with a predetermined filter characteristic, the predetermined filter characteristic based on the selected acoustic manipulation parameter.

14. The device of claim 12, wherein the acoustic detail manipulation unit includes a filter configured to sub-sample the auditory stream at a predetermined sampling rate, the predetermined sampling rate based on the selected acoustic manipulation parameter.

15. The device of claim 12, wherein the acoustic detail manipulation unit includes a noise generator configured to add noise having a predetermined noise characteristic to the auditory stream, the predetermined noise characteristic based on the selected acoustic manipulation parameter.

16. The device of claim 12, wherein the acoustic detail manipulation unit includes:
a speech recognizer configured to convert the auditory stream to a text representation; and
a speech synthesizer configured to convert the text representation to a speech production voice, the speech production voice having a predetermined speech characteristic based on the selected acoustic manipulation parameter.

17. The device of claim 12, wherein the predetermined acoustic detail characteristic includes at least one of a pitch, a harmonic, an intonation, a transient sound, a sibilant sound or frequency dynamics of the stimulus.

18. The device of claim 12, further comprising a microphone coupled to the audio input interface, the microphone configured to capture the auditory stream.

19. The device of claim 12, wherein the audio input interface is configured to receive the auditory stream from a remote device, the remote device including at least one of a phone, a computer, a television, and a playback device having an audio capability.

20. The device of claim 12, wherein the device is configured to be calibrated based on at least one predetermined stimulus presented to the ASD individual via the at least one loudspeaker and one or more measured brain responses of the ASD individual acquired synchronous with the presented at least one predetermined stimulus.

21. The device of claim 12, wherein the storage device is further configured to store one or more predetermined sound stimuli for calibration of the device.

22. The device of claim 18, wherein the audio input interface further comprises an analog-to-digital converter for converting an audio signal from the microphone to a digital signal.

* * * * *